US009545110B2

(12) United States Patent
Probasco et al.

(10) Patent No.: US 9,545,110 B2
(45) Date of Patent: *Jan. 17, 2017

(54) COMPOSITIONS AND METHODS FOR CONTROLLING A HONEY BEE PARASITIC MITE INFESTATION

(71) Applicant: John I. Haas, Inc., Washington, DC (US)

(72) Inventors: Gene Probasco, Yakima, WA (US); Lloyd Schantz, Washington, DC (US); Mark M. Bossert, Yakima, WA (US)

(73) Assignee: JOHN I. HAAS, INC., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/758,392

(22) PCT Filed: Jan. 6, 2014

(86) PCT No.: PCT/US2014/010347
§ 371 (c)(1),
(2) Date: Jun. 29, 2015

(87) PCT Pub. No.: WO2014/107664
PCT Pub. Date: Jul. 10, 2014

(65) Prior Publication Data
US 2015/0366215 A1    Dec. 24, 2015

Related U.S. Application Data

(60) Provisional application No. 61/749,727, filed on Jan. 7, 2013.

(51) Int. Cl.
| A01K 51/00 | (2006.01) |
| A01N 65/00 | (2009.01) |
| A61K 35/64 | (2015.01) |
| A01N 61/00 | (2006.01) |
| A01N 65/08 | (2009.01) |
| A01K 47/04 | (2006.01) |
| A01N 25/08 | (2006.01) |
| A01M 1/20 | (2006.01) |

(52) U.S. Cl.
CPC .............. *A01N 61/00* (2013.01); *A01K 47/04* (2013.01); *A01K 51/00* (2013.01); *A01M 1/2011* (2013.01); *A01M 1/2022* (2013.01); *A01M 1/2055* (2013.01); *A01N 25/08* (2013.01); *A01N 65/08* (2013.01)

(58) Field of Classification Search
CPC ........ A01N 65/00; A01N 61/00; A01K 51/00; A01K 47/06; A01M 1/2011
See application file for complete search history.

(56) References Cited

U.S. PATENT DOCUMENTS

| 3,615,660 A | 10/1971 | Bavisotto et al. |
| 3,781,425 A | 12/1973 | Martin et al. |
| 4,002,683 A | 1/1977 | Todd, Jr. |
| 4,148,873 A | 4/1979 | Owades |
| 4,170,638 A | 10/1979 | Owades |
| 4,281,061 A | 7/1981 | Zuk et al. |
| 4,299,816 A | 11/1981 | Polyakov et al. |
| 4,562,794 A | 1/1986 | Speckman |
| 4,682,380 A | 7/1987 | Martin |
| 4,775,534 A | 10/1988 | Bartlett et al. |
| 4,837,216 A | 6/1989 | Mehlhorn et al. |
| 4,844,939 A | 7/1989 | Todd, Jr. |
| 4,847,292 A | 7/1989 | Katz et al. |
| 4,867,731 A | 9/1989 | Willard et al. |
| 4,876,265 A | 10/1989 | Schmid |
| 4,965,287 A * | 10/1990 | Stendel .................. A01N 53/00 449/2 |
| 5,023,359 A | 6/1991 | Bounias et al. |
| 5,069,651 A | 12/1991 | Amdt |
| 5,070,091 A | 12/1991 | Mehlhorn et al. |
| 5,082,975 A | 1/1992 | Todd, Jr. et al. |
| 5,135,758 A | 8/1992 | Arnold et al. |
| 5,158,788 A | 10/1992 | Lavens et al. |
| 5,166,449 A | 11/1992 | Todd, Jr. et al. |
| 5,227,162 A | 7/1993 | Ferrari |
| 5,230,894 A | 7/1993 | Robert et al. |
| 5,286,506 A | 2/1994 | Millis et al. |

(Continued)

FOREIGN PATENT DOCUMENTS

| EP | 0212623 | 3/1987 |
| EP | 0339147 | 11/1989 |

(Continued)

OTHER PUBLICATIONS

International Search Report for PCT/US2014/010347 dated May 2, 2014.
Extended European Search Report dated Apr. 29, 2016, issued in connection with European Patent App. No. 14735165.4, 11 pages.
"ANR-1186 Small Hive Beetle Life Cycle What They Look Like Eggs to Adults in 45 Days," Mar. 1, 2001, XP55266758, http://www.aces.edu/pubs/docs/A/ANR-1186/ANR-1186.pdf—Alabama A&M and Auburn Universities.

(Continued)

*Primary Examiner* — Frederick Krass
*Assistant Examiner* — Tracy Liu
(74) *Attorney, Agent, or Firm* — Miller Nash Graham & Dunn LLP; Chandra E. Eidt

(57) ABSTRACT

As described below, the present invention features methods and compositions for controlling a honey bee parasitic mite or for the treatment or prevention of a parasitic mite infestation in a honey bee hive. In particular embodiments, the invention provides a miticidal delivery device, wherein the device is a corrugated strip comprising a liquid composition comprising at least about 15% potassium salts of hop beta acids, solvent and an emulsifier.

26 Claims, 5 Drawing Sheets

(56) References Cited

U.S. PATENT DOCUMENTS

| | | | |
|---|---|---|---|
| 5,312,622 A | 5/1994 | Nagy et al. | |
| 5,348,511 A | 9/1994 | Gross et al. | |
| 5,370,863 A | 12/1994 | Barney et al. | |
| 5,372,817 A | 12/1994 | Locke et al. | |
| 5,455,038 A | 10/1995 | Barney et al. | |
| 5,583,262 A | 12/1996 | Maye et al. | |
| 5,624,701 A | 4/1997 | Maye et al. | |
| 5,750,129 A | 5/1998 | Wakarchuk | |
| 5,827,895 A | 10/1998 | Nutter et al. | |
| 5,849,317 A | 12/1998 | Shorey et al. | |
| 6,010,390 A | 1/2000 | Harper | |
| 6,037,374 A | 3/2000 | Kochansky et al. | |
| 6,083,254 A | 7/2000 | Evans et al. | |
| 6,096,350 A | 8/2000 | Kemp et al. | |
| 6,204,283 B1 | 3/2001 | Black et al. | |
| 6,221,375 B1 | 4/2001 | Howse | |
| 6,251,461 B1 | 6/2001 | Johnson et al. | |
| 6,277,371 B1 | 8/2001 | Haragsim et al. | |
| 6,419,943 B1* | 7/2002 | Sakurada | A01M 1/02 424/409 |
| 6,450,858 B1* | 9/2002 | Schmitz | A01K 47/06 449/20 |
| 6,451,365 B1 | 9/2002 | King et al. | |
| 6,468,129 B1 | 10/2002 | Griffith | |
| 6,475,061 B1 | 11/2002 | Huang | |
| 6,475,537 B1* | 11/2002 | King | A23L 3/3472 424/405 |
| 6,476,015 B1 | 11/2002 | Turos et al. | |
| 6,585,557 B1 | 7/2003 | Remon et al. | |
| 6,595,828 B2 | 7/2003 | Page, Jr. et al. | |
| 6,620,025 B2 | 9/2003 | Scheuneman et al. | |
| 6,620,446 B2 | 9/2003 | King et al. | |
| 6,646,014 B2 | 11/2003 | Watkins et al. | |
| 6,702,645 B2 | 3/2004 | Vanderpool | |
| 6,820,773 B1 | 11/2004 | Orth | |
| 6,837,770 B2 | 1/2005 | Ruzicka | |
| 6,843,985 B2 | 1/2005 | Erickson, Jr. et al. | |
| 7,087,849 B2 | 8/2006 | Brown et al. | |
| 7,137,864 B2 | 11/2006 | Swanson | |
| 7,879,348 B2* | 2/2011 | Volby | A01N 25/34 424/405 |
| 2001/0014346 A1 | 8/2001 | Watkins | |
| 2002/0034529 A1* | 3/2002 | Prince | A01K 51/00 424/405 |
| 2002/0051804 A1 | 5/2002 | Probasco et al. | |
| 2002/0094756 A1 | 7/2002 | Labesque | |
| 2002/0151249 A1 | 10/2002 | Scheuneman et al. | |
| 2002/0182977 A1 | 12/2002 | Page, Jr. et al. | |
| 2003/0010817 A1* | 1/2003 | Lingle | B31B 43/00 229/406 |
| 2003/0027490 A1 | 2/2003 | Wilkinson | |
| 2003/0032669 A1 | 2/2003 | Verbruggen et al. | |
| 2003/0044443 A1 | 3/2003 | Erickson, Jr. et al. | |
| 2003/0060379 A1 | 3/2003 | Souter et al. | |
| 2003/0154508 A1 | 8/2003 | Stevens et al. | |
| 2003/0190860 A1 | 10/2003 | Vanderpool | |
| 2003/0215535 A1 | 11/2003 | Wilson et al. | |
| 2003/0228814 A1 | 12/2003 | Barney et al. | |
| 2004/0077291 A1 | 4/2004 | Arthur et al. | |
| 2004/0131709 A1 | 7/2004 | Berdahl et al. | |
| 2004/0175480 A1 | 9/2004 | Seman et al. | |
| 2004/0229542 A1 | 11/2004 | Ruzicka | |
| 2005/0031743 A1 | 2/2005 | Areso | |
| 2005/0043404 A1 | 2/2005 | Probasco et al. | |
| 2005/0048093 A1 | 3/2005 | Milani et al. | |
| 2005/0049230 A1 | 3/2005 | Henrich et al. | |
| 2005/0090560 A1 | 4/2005 | Erickson, Jr. et al. | |
| 2005/0095954 A1 | 5/2005 | Castillo | |
| 2005/0220914 A1 | 10/2005 | Probasco et al. | |
| 2006/0008492 A1 | 1/2006 | Janowicz et al. | |
| 2006/0009122 A1 | 1/2006 | Swanson | |
| 2006/0009211 A1 | 1/2006 | Sato | |
| 2006/0013870 A1 | 1/2006 | Kuhrts | |
| 2006/0141904 A1 | 6/2006 | Teal et al. | |
| 2007/0026765 A1 | 2/2007 | Renn | |
| 2007/0059333 A1 | 3/2007 | Volby | |
| 2007/0232188 A1 | 10/2007 | Probasco | |
| 2007/0248549 A1 | 10/2007 | Kuhrts | |
| 2008/0026673 A1 | 1/2008 | Probasco | |
| 2009/0104288 A1 | 4/2009 | Probasco | |
| 2010/0087121 A1* | 4/2010 | Probasco | A01K 51/00 449/61 |
| 2010/0227010 A1* | 9/2010 | Jones | A01N 37/02 424/747 |
| 2013/0145679 A1 | 6/2013 | Nenninger | |

FOREIGN PATENT DOCUMENTS

| | | |
|---|---|---|
| EP | 0441750 | 8/1991 |
| EP | 0681029 | 11/1995 |
| EP | 0816430 A2 | 1/1998 |
| EP | 0824093 | 2/1998 |
| GB | 592090 A | 9/1947 |
| GB | 1058975 | 2/1967 |
| GB | 2330076 | 4/1999 |
| JP | 50024244 | 3/1975 |
| JP | 57080304 | 2/1982 |
| WO | 9409759 | 5/1994 |
| WO | 9733971 | 9/1997 |
| WO | 9909842 | 3/1999 |
| WO | 0106877 | 2/2001 |
| WO | WO-2007037905 A2 | 4/2007 |
| WO | 2008060591 | 5/2008 |
| WO | 2009098300 | 8/2009 |
| WO | 2009099646 | 8/2009 |
| WO | 2010131058 | 11/2010 |
| WO | WO-2012170420 A2 | 12/2012 |
| WO | 2013185059 A2 | 12/2013 |

OTHER PUBLICATIONS

Nordenfors, Helena and Hoglund, Johan and Uggla, Arvid, "Effects of Temperature and Humidity on Oviposition, Molting, and Longevity of Dermanyssus gailinae (Acari: Dermanyssidae)," Journal of Medical Entomology, Jan. 1, 1999, pp. 68-68, XP55266744.
"Culpeper's Complete Herbal A book of Natural Remedies for Ancient Ills," Wordsworth Reference, pp. 134-135 (1995).
Jones, G., "Potential Control of Two-Spotted Spider Mite, Tetranychus urticae Koch, Using Hop β-Fraction," (1998) pp. 1-165, A thesis submitted for the degree of Doctor of Philosophy of the University of London and for the Diploma of Imperial College of Science, Technology & Medicine.
Jones et al., "Repellant and Ovipositon-Deterring Effects of Hop-Beta Acids on the Two-Spotted Spider Mite Tetranychus Urticae," Pesticide Science, vol. 47, No. 2, pp. 165-169 (1996).
Losel et al., "The Potential of Semiochemicals for Control of Phorodon Hummuli (Homoptera; Aphididae)," Pesticide Science, vol. 48, No. 4, pp. 293-303 (1996).
Sutherland, Carol A., "Spider Mites," New Mexico State University O & T Guide, http://aces.nmsu.edu/ces/plantclinic/documents/o-08-spidermites.pdf , p. 2.
"Varroa Mites," Mid-Atlantic Apiculture Research and Extension Consortium, MAAREC Publication 4.7; http://maarec.psu.edu/pdfs/TRACHEAL.pdf , p. 1.
"Tracheal Mites," Mid-Atlantic Apiculture Research and Extension Consortium, MAAREC Publciation 4.2; http://maarec.psu.edu/pdfs/TRACHEAL.PDF , p. 1.
Kaneda et al., Beer Adsorption on a Lipid Membrane as Related to Sen Evaluation), 2001, http://www.asbcnet.org/journal/pdfs/2001/0912-04R.pdf (Abstract Only).
"Antibiotics: Antibacterial Agents," retrieved from the internet http://users.rcn.com/jkimball.ma.ultranet/BiologyPages/A/Antibiotics.html.
Rusty, "HopGuard: the new Varroa pesticide," Honey Bee Suite, Nov. 11, 2010, Online document obtained from http://honeybeesuite.com/hopguard-the-new-varroa-pesticide/.
Priebe, D.L., "Hopguard Section 18 Specific Exemption" BetaTec hop products, created Feb. 23, 2011 Online document obtained from http://pested.osu.edu/documents/Section%2018/HopGuardFinalContainer.

(56) References Cited

OTHER PUBLICATIONS

BetaTecHopProducts' channel, "HopGuard—Varroa Mite Control", YouTube, Uploaded on Mar. 5, 2011, Online document obtained from http://www.youtube.com/watch?v=T2y4mdPhlo.

Extended European Search Report issued Oct. 20, 2015 in connection with European Patent App. No. 13800867.7

Chapter 2.2.6: Tropilaelaps infestation of honey bees (*Trooilaelaps* spp.). OIE Terrestrial Manual 2008: 419-423. http://www.oie.int/fileadmin/Home/eng/Health_standards/tahm/2.02.06_TROPILAELAPS.pdf.

Sharma et al., "Efficacy of some acaricides against extoparasitic mite *Tropilaelaps clareae* infesting European honey bee *Apis mellifera*." Indian J. Agric. Res. Mar. 1, 2003, 37(1):60-3.

Degrandi-Hoffman, G. et al., "The Effects of Beta Acids From Hops (*Humulus lupulus*) on Mortality of Varroa Destructor (*Acari: Varroidae*)"; Experimental and Applied Acarology, Jul. 6, 2012, vol. 58, pp. 407-421.

Extended European Search Report issued May 21, 2015 in connection with European Patent Application No. 12796924.4.

Partial Supplementary European Search Report issued Jan. 28, 2015 in connection with European Patent Application No. 12796924.4.

Newsletter of the Bayside Brewers Club, http://www.home.alone.net.au/bbc/bbcmay.html, pp. 1-7, May 1996.

Haas Products & Applications http://www.john-i-haas.com/products/getinfo_products.htm?prod=isohop, 2001.

Sammataro et al., Parasitic Mites of Honey Bees: Life History, Implications, and Impact, Annu. Rev. Entomol 2000 45:519-548.

Haas Isohop Product Information—http://www.gne22.dial.pipex.com/isohop.html.

Simpson, W.J. "Synergism Between Hop Resins and Phosphoric Acid and Its Relevance to the Acid Washing of Yeast", J. Instr. Brew., Sep.-Oct. 1987, vol. 93, pp. 405-406.

Simpson, W.J. "Studies on the Sensitivity of Lactic Acid Bacteria to Hop Bitter Acids", J. Inst. Brew., Sep.-Oct. 1993, vol. 99, pp. 405-411.

\* cited by examiner

Figure 1A Standard Hop Guard
Figure 1B
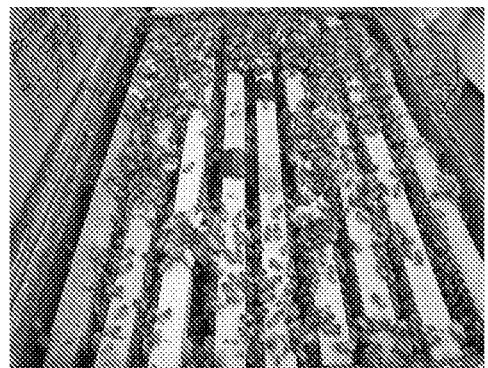

COMPOSITIONS AND METHODS FOR CONTROLLING A HONEY BEE PARASITIC MITE INFESTATION

CROSS-REFERENCE TO RELATED APPLICATIONS

This application is the national phase under 35 U.S.C. §371 of PCT International Application No, PCT/US2014/010347, filed Jan. 6, 2014, which claims the benefit of U.S Provisional Patent Application No, 61/749,727, filed Jan. 7, 2013 the entire contents of the aforementioned applications are hereby incorporated herein by reference.

BACKGROUND OF THE INVENTION

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*. *Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as *Melissococcus pluton*, which causes European foulbrood. In addition, to their parasitic effects, *Varroa* mites are suspected to act as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality. Maintaining a supply of strong honey bee colonies available for pollination is essential for the sustained production of farm crops worth more than $14 billion to U.S. agriculture. During the winter of 2004-2005, an estimated 40% of the honey bee colonies in the U.S. were weakened or collapsed due to *Varroa* infestation. Current methods of treating *Varroa* infestations are proving to be ineffective as the mites develop resistance to existing miticides. In addition, the use of such miticides may introduce injurious chemicals into honey that is intended for human consumption. New compositions and methods for treating or preventing *Varroa* mite infestations are urgently required. Desirably, such compositions would include only natural ingredients that pose no risk to human health.

SUMMARY OF THE INVENTION

As described below, the present invention features methods and compositions for controlling a honey bee parasitic mite or for the treatment or prevention of a parasitic mite infestation in a honey bee hive.

In one aspect, the invention features a corrugated strip for use in reducing a honey bee parasitic mite infestation, the strip comprising a liquid composition comprising at least about 15% beta acids, a solvent, and an emulsifier. In one embodiment, the liquid composition comprises potassium salts of hop beta acids. In another embodiment, the liquid composition comprises hop beta acid resins. In another embodiment, the liquid composition is a solution or an emulsion. In another embodiment, the liquid composition comprises between about 30-35% by weight propylene glycol, about 30-35% by weight monooctadecanoate, and about 30-35% hop beta acid resins. In another embodiment, the liquid composition comprises equal parts hop beta acid resins, propylene glycol, and polysorbate 60. In another embodiment, the strip comprises paper, cardboard, or another paper pulp based material. In another embodiment, the strip is between about 1 and 3 mm thick and has between about 5 and 8 flutes per inch.

In another aspect, the invention features a corrugated strip prepared by soaking an absorbent strip in a liquid composition comprising hop beta acids.

In yet another aspect, the invention features a foil package prepared by soaking an absorbent corrugated strip in a liquid composition comprising hop beta acids, and packaging the corrugated strip and liquid in a moisture resistant package.

In yet another aspect, the invention features a man-made hive comprising the corrugated strip of any of the above-aspects or any other embodiment of the invention delineated herein.

In still another aspect, the invention features a honey bee product produced in the hive of the above-aspect.

In yet another aspect, the invention features a method of reducing a honey bee parasitic mite infestation in a honey bee hive, the method comprising contacting a hive with the corrugated strip of any of the above-aspects, thereby reducing a bee parasitic mite infestation in the hive. In one embodiment, the method involves providing 2 corrugated strips/10 frames. In another embodiment, the corrugated strips are hung from a frame within the hive.

In yet another aspect, the invention features a kit for the treatment or prevention of a parasitic mite infestation, the kit comprising the strip of any the above-aspects or any other embodiment of the invention delineated herein. In one embodiment, the strip is packaged in a moisture resistant material.

Other features and advantages of the invention will be apparent from the detailed description, and from the claims.

DEFINITIONS

By "acarid" is meant an arachnid of the order Acarina, which includes mites and ticks.

By "alpha acid" is meant an organic acid derived from a hop plant (*Humulus lupulus*) having structural homology to a humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to a lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydro hulupones.

By "biological function" is meant any physiological or behavioral activity of an organism. Exemplary biological functions include reproduction, respiration, neural activity, locomotion. Honey production is a biological function that is specific to a honey bee.

In this disclosure, "comprises," "comprising," "containing" and "having" and the like can have the meaning ascribed to them in U.S. Patent law and can mean " includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "contacting" is meant touching, associating with, or having proximity to a composition. For example, a hop derivative may contact a hive either inside or outside of the hive structure.

By "controlled release" is meant released over the course of hours, days, weeks, or months.

By "controlling a parasitic mite" is meant inhibiting mite survival or reducing, slowing, or stabilizing the growth of a mite population.

By "comb" is meant sections of hexagonal bee wax cells that are used to rear honey bee progeny ("brood") and store honey and pollen.

By "effective amount of a miticide" is meant an amount effective to disrupt a mite biological function.

By "emulsion" is meant a mixture comprising at least two immiscible liquids. Typically, one of the liquids is dispersed in small droplets in the second liquid. Preferably, the emulsion is a stable emulsion where the two phases remain stably mixed for hours, days, or weeks. The emulsion may or may not contain an added emulsifier.

By "hive" is meant a man-made structure that contains a bee colony. A modern box hive typically includes a bottom board, cover, and one or more boxes, stacked one above the other. Inside, each box contains a series of movable frames of comb or foundation held in a vertical position a bee space apart.

By "honey bee" is meant a Hymenopteran insect of the genus *Apis*. The term "honey bee" is not limited to the adult form of the insect, but encompasses all honey bee developmental stages, including but not limited to egg, larva, and pupa. Exemplary honey bee species include *Apis mellifera* and *Apis cerana*.

By "honey bee colony" is meant a community of bees. Honey bee colonies may occur in the wild or may be maintained by bee keepers.

By "honey bee parasitic mite" is meant any acarid that parasitizes a honey bee or infests a honey bee hive. Exemplary honey bee parasitic mites include *Varroa* mites and tracheal mites.

By "hop derivative" is meant any molecule that naturally occurs in hops (*Humulus lupulus*) and chemical derivatives thereof. Hop derivatives (e.g., alpha acids, beta acids) may be purified from hops or may be chemically synthesized.

By "infestation" is meant the colonization of a site or the parasitization of an organism by a pest.

By "isolated hop acid" is meant a hop acid of the invention that has been separated from one or more components that naturally accompany it in its native state. An isolated hop acid of the invention may be obtained, for example, by extraction from a natural source or by chemical synthesis. Purity can be measured by any appropriate method, for example, column chromatography, spectrophotometry, polyacrylamide gel electrophoresis, or by HPLC analysis.

By "miticide" is meant an agent that inhibits a biological function of a mite.

By "miticidal activity" is meant any activity that inhibits the growth, reproduction, or survival of a mite or other acarid.

By "nucleus colony" is meant a package suitable for shipment comprising at least one queen, one or more bees, a honey frame, and a frame comprising brood. "Brood" refers to any one or more of egg, embryo, larva and pupal stages that develops within a bee hive. Typically, the nucleus colony is packaged in a box, crate, or other container suitable for shipment via courier or mail.

By "packaged bees" is meant a package suitable for shipment comprising at least one queen and one or more honey bees. Typically, packaged bees comprise a mated and/or laying queen and a number of bees (e.g., 1 lb, 2 lb, 3 lb, or more). The package is suitable for shipment via courier or mail.

By "preventing a mite infestation" is meant reducing the success that a mite infestation will be established in an *Apis* colony.

By "treating a mite infestation" is meant reducing, stabilizing, or slowing the growth of a mite population in an *Apis* colony.

BRIEF DESCRIPTION OF THE DRAWINGS

FIGS. 1A and 1B are photographs of standard Hop-Guard® strips being used to treat hives.

DETAILED DESCRIPTION OF THE INVENTION

Figure 2:
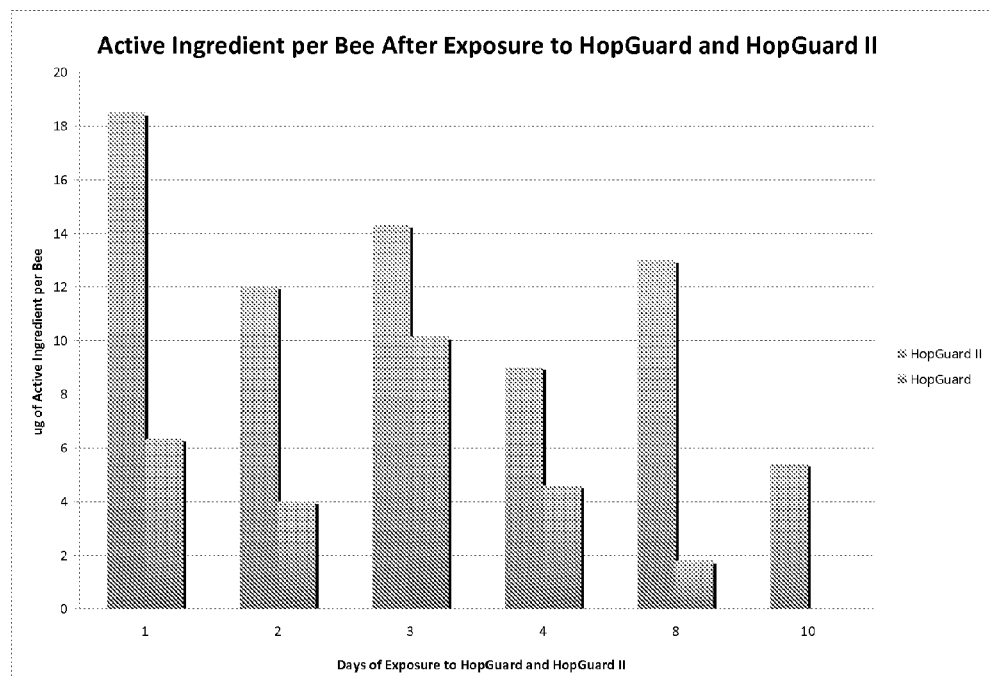
FIG. 2 is a graph showing beta acids per bee measured over a 10-day course of treatment with standard HopGuard® or HopGuard II®®.

The present invention provides improved delivery devices that are useful for the treatment or prevention of honey bee parasitic mite infestations (e.g., *Varroa* mites, tracheal mites).

In one embodiment, the invention provides a corrugated strip comprising a liquid composition comprising hop beta acids for use in treating or preventing a mite infestation in a honey bee hive. In one embodiment, the corrugated strip comprises equal parts beta acid resins, solvent (e.g. propylene glycol), and an emulsifier (e.g., polysorbate). In one embodiment, the beta acid resins comprise at least about 15% potassium salts of beta acids and other extractives. Preferably the corrugated strip is moistened with a solution or stable emulsion comprising equal parts beta acid resins dispersed in propylene glycol or another solvent and polysorbate-60 or another emulsifier for at least about 24-hours or until the desired saturation point is reached. The moistened corrugated strips are packaged for delivery to apiaries. The moistened corrugated strips are hung within the hive where they come in contact with the honey bees, which are infested with parasitic mites. The beta acids kill parasitic mites on contact, and the honey bees disperse the hop beta acids throughout the honey bee hive. As reported in detail below, the corrugated strips of the present invention were surprisingly effective in delivering more hop beta acids to more bees and remained effective for a longer period of time than when the hop beta acids were delivered on conventional strips. This improved delivery resulted in greater efficacy in reducing the parasitic mite infestation of the hive.

*Apis*

Honey bees are insects that pass through four life stages: the egg, larva, pupa and adult. Adult bees belong to one of three castes: queen, worker, or drone. The queen bee is the only female in the colony that is capable of reproduction and is responsible for all egg production. The worker bees are non-reproductive females who gather honey and care for the queen's progeny, or "brood." The drones are male bees that mate with the queen. The life cycle, from egg to adult bee, takes twenty-one days for worker bees and twenty-four days for drones. The queen bee lays each egg in a single cell of the comb. The egg generally hatches into a larva on the fourth day, which continues its development within the cell. On the ninth day the cell with the developing larva is capped with wax and the larva undergoes pupal metamorphosis. On day twenty-one, a new adult worker bee emerges.

Acarids

Acarids are small parasitic arachnids that act as parasites on a variety of plants and animals, including honey bees. Parasitic mites that prey on honey bees include *Varroa* mites (e.g., *Varroa destructor, Varroa jacobsoni*) and tracheal mites (e.g., *Acarapis woodi*). Tracheal mites are microscopic mites that inhabit the respiratory tubes of bees. *Varroa* mites are ectoparasites that feed on bee hemolymph, and infest wild and domestic honey bee colonies. *Varroa* mite reproduction begins when the adult female mite enters a brood cell shortly before it is capped. Drone brood, which is reared in larger cells than worker brood, is preferentially targeted for mite infestation. The female mite feeds on the larval hemolymph prior to depositing her eggs. The *Varroa* eggs eclose under the sealed cell, and the developing mites feed on the bee pupa. The first egg laid by the female *Varroa* develops into a male. Subsequent eggs develop into females that mate with their brother. The mated female mites along with their mother are released from the capped cell when the bee emerges. The female mites typically attach to adult bees between the abdominal segments or between body regions, where they feed on the bees' hemolymph. Adult bees serve as intermediate hosts and as a means of transport to new sites of infestation.

Desirably, miticides used in acarid control should address the following four needs: i) should disrupt a physiological function required for mite survival; ii) should cause no adult bee mortality; iii) should have no adverse effects on human bee keepers or honey intended for human consumption; and iv) should be capable of delivery into the hive.

Mite Control

Products used to control honey bee parasitic mite infestation reduce, stabilize, or slow the growth of a mite population in a hive or inhibit the growth, survival, reproduction, or other biological function of a honey bee parasitic mite. Preferably, the miticide kills the mite. Methods for measuring parasitic mite infestation are known in the art. A number of parameters can be indicative of the level of infestation present in a bee colony: the number of mites present in a sample of bees from an infested hive can be used as one measure of the level of infestation present in the hive; bees reared in a hive having an active infestation are on average smaller than bees reared in a hive without infestation; thus, bee size or weight can be used as another measure of infestation; the amount of honey produced in an infected hive may be less than that produced in a healthy hive; accordingly, honey production could serve as yet another measure of the level of infestation; and finally, severe infestations result in complete loss of colonies. Thus, loss of colonies can be a measure of the level of infestation present in the hive.

Methods for measuring parasitic mite infestation are known in the art. A number of parameters can be indicative of the level of infestation present in a bee colony: the number of mites present in a sample of bees from an infested hive can be used as one measure of the level of infestation present in the hive; bees reared in a hive having an active infestation are on average smaller than bees reared in a hive without infestation; thus, bee size or weight can be used as another measure of infestation; the amount of honey produced in an infected hive may be less than that produced in a healthy hive; accordingly, honey production could serve as yet another measure of the level of infestation; and finally, severe infestations result in complete loss of colonies. Thus, loss of colonies can be a measure of the level of infestation present in the hive.

In one example, drone brood sampling can be carried out. Capped drone brood are removed from the hive and examined for *Varroa* mites, which are easily visualized against the white pupae. This method measures the percentage of brood that's infected with *Varroa* mites. Natural mite drop onto a sticky board is the most common method used to monitor *Varroa* mites. A sticky or Vaseline-coated board is placed on the floor of the hive, usually with a wire mesh screen on top to keep the bees off the sticky board, and the board is left in place for a set period of time. After 1-3 days, the board is removed and the beekeeper counts the number of mites that are on the sticky board. The 24-hour mite drop provides a measure of the level of hive infestation. Alternatively, the board is left in place for 2, 3, or more days and the average number of mites dropped per day is measured.

Powdered sugar sampling is the third common method of monitoring varroa mite populations. In this method, a sample of approximately 300 live nurse bees (½ cup of bees) is scooped up in a jar and shaken gently with powdered sugar for about one minute. The sugar causes the mites to fall off the bees, and the mites are dumped out into a light-coloured dish to be counted. The number of mites per bee—or mites per ½ cup sample provides a measure of the level of infestation.

Alternatively, the sampled bees are killed with a wash of alcohol or soapy water and the sample poured through a double strainer. A coarse mesh catches the bees but allows the mites to pass through, while a second finer screen catches the mites and allows the liquid to flow away. The mites present in the sample are then counted.

In one embodiment, a miticide of the invention reduces the level of infestation in a hive by at least 10%, 25%, 50%, 75% or even by 100%. In another embodiment, a miticide of the invention induces at least 50%, 60%, or 70% increase in mite drop relative to an untreated hive. Preferably, the miticide induces 75%, 80%, 90%, or even 95% or 100% increase in mite drop relative to the level prior to treatment. Screening methods are used to identify concentrations of hop derivatives that will be lethal to a mite (e.g., induce at least 70% mite lethality) while minimizing lethal effects on adult bees.

Alternatively or in addition, a miticide of the invention inhibits mite reproduction. Preferably, the miticide reduces mite reproduction by at least 25%, 50%, 75% or 100%. In another approach, the miticide disrupts a biological function required for acarid locomotion; such treatment allows the mite to be trapped, drowned, isolated, or otherwise removed from an area. The invention further provides for mite control in packaged bees and nucleus colonies. Packaged bees and nucleus colonies typically comprise a mated queen and a number of honey bees (e.g., 1, 2, 3, 4, 5 lbs). Packaged bees and nucleus colonies are typically shipped to an end user (e.g., a bee keeper) for use in starting, expanding, or replacing one or more bee hives. Because many bee colonies are infested with honey bee parasitic mites, the shipment of packaged bees and nucleus colonies can spread or increase infestation. Treating packaged bees and nucleus colonies with a composition of the invention can reduce or even eliminate mite infestation in the package or nucleus. In one embodiment, the package or nucleus comprises a strip of the invention. In another embodiment, some portion of the package or container is impregnated with a composition comprising an isolated hop acid or hop acid derivative (e.g., hop beta acids).

Miticide Screening

Commercial products that are currently being used to control mite infestation can be lethal to adult bees when administered at high concentrations, can have adverse effects on human bee keepers, and may contaminate honey intended for human consumption. Conventional miticides include Tau-Fluvalinate (a synthetic-pyrethroid compound used as a selective contact and stomach poison) and Coumaphos (a systemic organic phosphate) used on animals to control lice, ticks and mites. In contrast to conventional miticides, compositions of the invention contain safe natural products derived from hops. Hops have been used for centuries to flavor beer; thus, formulations comprising hop derivatives are generally safe. Miticidal compositions of the invention will not adversely affect human bee keepers or honey intended for human consumption.

Miticides of the invention contain concentrations of hop derivatives that have few or no adverse effects on honey bees during any of their life stages, but are effective in killing or disrupting the biological functioning of a mite. As reported herein, beta acids, a hop derivative, delivered at 4% concentration killed 87% of exposed mites after four hours while causing 0% lethality in adult bees. In one approach, mites are exposed to varying concentrations of hop derivatives to identify those concentrations that kill 50% to 100% of the exposed mite. Adult honey bees are then exposed to concentrations of hop derivatives having miticidal activity to identify those that have a minimal effect on honey bee survival. Preferably, at least 75%, 80%, 85%, 90%, 95%, or 100% of adult bees will survive following exposure to a miticidal composition. In a similar approach, the effect of hop derivatives on mite and honey bee reproduction is assessed. Screening assays are used to determine the concentration of a miticide that reduces the number of eggs laid by the female mite, reduces the number of eggs that hatch, or reduces the number of mites that grow to reproductive maturity; preferably, the reduction is by at least 25%, 50%, 75%, 85%, 95% or 100%.

Hop Derivatives

A hop derivative is a compound that occurs naturally in a hop plant (*Humulus lupulus*) or is chemically derived (either through natural biosynthetic procesess (e.g., living organism metabolism (e.g., mammal, plant, bacteria)) or by synthetic processes using human intervention (e.g., chemical synthesis). Compositions of the invention include one or more compounds derived from hops. Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adlupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include beta acids, hexahydrobeta acids, rhoisoalpha acids, isoalpha acids, tetrahydroisoalpha acids, and hexahydroisoalpha acids. Compositions comprising hop derivatives are also available commercially. John I. Haas, Inc. products containing hop derivatives include Redihop®, Isohop®, Tetrahop Gold®, Hexahop Gold®, MgRIAA and MgBeta. The active ingredients in these products are beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids (MgBeta), respectively. For convenience, the identities of these products are also listed in Table 1.

TABLE 1

| Hop Derivatives | |
|---|---|
| Betacide ® | beta acids |
| Redihop ® | rhoisoalpha acids |
| Isohop ® | isoalpha acids |
| Tetrahop Gold ® | tetrahydroisoalpha acids |
| Hexahop Gold ® | hexahydroisoalpha acids plus tetrahydroisoalpha acids |
| MgBeta | magnesium salt of beta acids |
| MgRIAA | magnesium salt of rhoisoalpha acids |
| MgTetrahop Gold ® | mg salt of tetrahydroisoalpha acids |
| MgHexahop Gold ® | mg salt of hexahydroisoalpha acids |

These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, countercurrent extraction, turbo-extraction, or by supercritical carbon-dioxide (temperature/pressure) extraction. The extract may then be further evaporated and thus concentrated to yield by means of air drying, spray drying, vacuum oven drying, fluid-bed drying or freeze-drying, the extract product.

Crude extracts are tested for miticidal activity as described herein. Further fractionation of a positive lead extract having miticidal activity is necessary to isolate chemical constituents responsible for the observed effect. Thus, the goal of the extraction, fractionation, and purification process is the careful characterization and identification of a chemical entity within the crude extract that disrupts a mite biological function. Methods of fractionation and purification of such heterogeneous extracts are known in the art. If desired, compounds shown to be useful as miticides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

In particular, after at least 1 year of storage, the compositions of the invention were found to retain at least about 95%-100% of the hop acids present at the time of application.

Water soluble hop acid alkali metal salts (e.g., sodium, potassium, lithium salts) and water insoluble hop acid alkaline earth metal salts (e.g., calcium, magnesium) are typically present in a diluent or carrier at levels ranging from about 0.1% to about 95%. The methods herein contemplate administration of an effective amount of compound or compound composition to achieve the desired or stated miticidal effect. Preferably, the amount of active ingredient (e.g., hop acid alkali metal salts, hop acid alkaline earth metal salts or combinations thereof) are combined with carrier materials (e.g., maltodextrin, cluster dextrin, corn starch, corn syrup solids, glucose, cyclodextrin, arabic gum, calaginan, inuline, partially hydrogenated soybean oil, cellulose, hydroxymethyl cellulose, hydroxyethyl cellulose, hydroxypropyl cellulose, rosin, hypomellose) to form a powder suitable for delivery. For some applications, miticides of the invention are formulated as liquids using diluents (e.g., sucrose or glucose solutions, water, juices, other aqueous solutions, water miscible solvents (ethanol, cremophor, dimethylsulfoxide (DMSO), dimethylformamide (DMF), isopropanol (IPA) or glycerol, and other solvents)) to form a solution or slurry.

A typical miticidal preparation will contain from about 1% to about 95% hop acid, where the bottom of the range is any integer between 5 and 94 and the top of the range is any integer between 6 and 95, where the hop acids are provided in a carrier (e.g., maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, hypomellose) that is suitable for use in methods of producing a product having miticidal activity. Where non-aqueous miticidal compositions are desired, the miticidal of the invention are preferably formulated with rosin or partially hydrogenated soybean oil. Such compositions may be used for the slow release of the active miticidal composition, for example, in an aqueous slurry. In still other embodiments, miticidal compositions of the invention are dispersed in cellulose powder. In each of the aforementioned embodiments, the hop acid alkali metal (e.g., sodium, potassium, lithium), alkaline earth metal salts (e.g., calcium, magnesium), or other hop acid salts are dispersed or dissolved in water, ethanol, or another diluent together with any one or more of maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, and hypomellose. The composition is then spray dried to facilitate the formation of particles less than 1 mm in size. Preferably, the conditions used for spray drying are adjusted such that the particles are at least about 1 µm, 5 µm, 10 µm, 25 µm, 50 µm, 75 µm, 100 µm, 150 µm, 200 µm, 500 µm, 1 mm, 2 mm, or 5 mm in size. The ratio of hop acids to carrier ranges between about 1:2 and 1:100 . Preferred ratios include 1:2, 1:3, 1:4, 1:5, 1:6, 1:7, 1:8, 1:9, 1:10, 1:20, 1:30, 1:50, 1:75, and 1:100 . Alternatively, compositions of the invention include at least about 1%, 10%, 20%, 30%, 50%, 60%, 75%, 80%, 90%, or 95% hop acid alkali metal (e.g., sodium, potassium, lithium) or hop acid alkaline earth metal salts (e.g., calcium, magnesium) in a diluent or carrier. Not all of the hop acids need be in the metal form. Anywhere between 5% and 100% of the hop acids present in the composition are in the metal form at any given time, and between 95% and 0% are present as free acids. In various embodiments, a composition of the invention contains hop acids where 90% are present in the metal form and 10% are present in the acid form; 50% are present in the metal form and 50% in the acid form; and 10% are present in the metal form and 90% in the acid form.

In preferred embodiments, the preparation includes between 1 and 95% (e.g., 1, 2, 3, 4, 5, 6, 7, 8, 9, 10, 25%, 75%, 80%, 90%, 95%) hop acids in a carrier or diluent. Alternatively, such preparations contain from about 20% to about 80% hop acids. Compositions containing alpha or beta acids are manufactured by ordinary methods. Hop acids suitable for addition to products can be formulated as ordinary tablets, capsules, solids, liquids, emulsions, slurries, fine granules or powders, which are suitable for administration to products during their preparation, following preparation but prior to storage, or at any time prior to their sale to a vendor or consumer. Lower or higher amounts than those recited above may be required. The compositions delineated herein include the compounds of the formulae delineated herein, as well as additional miticidal agents if present, in amounts effective for inhibiting mite growth or survival. Miticidal compositions of the invention may be used in virtually any application where the inhibition of a mite is desired. For example, compositions of the invention are used to prevent, reduce, inhibit, slow or stabilize the growth, proliferation, or survival of a mite.

Lower or higher doses than those recited herein may be required to effectively kill mites without adversely affecting honey bees. Specific dosage and treatment regimens are determined empirically as described herein. Compositions of the invention are also useful for preventing the establishment of an acarid infestation, for treating an established acarid infestation, and for maintaining the health of a hive previously treated for an acarid infestation.

Formulations

Hop derivatives can be provided to bees or bee hives in a number of convenient formulations. In general, the invention provides a liquid composition that comprises equal parts beta acid resins, solvent (e.g. propylene glycol), and an emulsifier (e.g., polysorbate). In one embodiment, the beta acid resins comprise at least about 15% potassium salts of beta acids and other extractives. This liquid composition comprising hop beta acids as the active ingredient can be used to impregnate, for example, corrugated strips useful in treating a honey bee infestation in a hive.

Other strategies for dispersing a therapeutic or prophylactic agent within the hive rely on i) providing the agent in a food source (e.g., a liquid or solid food); ii) providing the agent in a composition that will induce hygienic behavior designed to remove the composition from the colony (a packet designed to be torn apart by the bees); or iii) providing the agent in a form that the bees will distribute throughout the colony (e.g., a tracking powder provided at an entrance to the hive). Formulations of the invention are used to target mites on the body of adult bees, in the brood cell, or in the hive. Desirably, the composition of the invention is active in the hive for at least forty-one days. This provides for the presence of the miticide for the entirety of the mite life cycle, which typically is completed over the course of twenty-one to thirty days. Where activity is maintained for a shorter period (e.g., seven, fourteen, twenty-one, or thirty days), repeated administration of a composition of the invention may be desired or required. Compositions that are active for longer periods (e.g., two, three, six, nine, or twelve months) are also envisioned. Such compositions may be used for the long-term treatment or prevention of a mite infestation.

Emulsions

Miticides of the invention can also be provided as emulsions or solutions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release. In one embodiment, hop beta acids (e.g., hop beta acid resins, potassium salts of hop beta acids) are dispersed in solvent (e.g., propylene glycol) to form an emulsion. If desired, the emulsion is stabilized using an emulsifier (e.g., polysorbate 60, lecithin). Emulsifiers are known in the art and described herein. One preferred product for use in treating a honey bee parasitic mite infestation is Hop-Guard®. HopGuard® is a liquid solution or emulsion that comprises 33.3% potassium hop beta acid resins, 33.3% propylene glycol, and 33.3% polysorbate-60 by weight. Preferably, hop beta acids are dispersed in a propylene glycol solvent with polysorbate-60 added as an emulsifier. Biodegradable corrugated strips comprising the emulsions are then delivered to the hive. The corrugated strips are moistened by contacting them with hop beta acid resins, propylene glycol and polysorbate-60.

Powdered Formulations

Current miticides are introduced into the beehive on plastic non-biodegradable corrugated strips that are about 1" wide, 9" long and ¼" thick. Similar means could be used for the delivery of hop derivatives. Other strip compositions include, but are not limited to, membranes, paper, plastic, and polymer corrugated strips. In one embodiment, a composition comprising a hop derivative is provided in a powdered formulation. A substrate material is coated with a powdered formulation of hop acids, and the coating is subsequently encased in a layer of a substance that is attractive to bees, such as powdered sugar. This strip is placed inside the beehive where the adult bees chew into the powdered sugar and expose the powdered hop acids. The powdered hop acids get onto the body of the adult bees, thereby contacting mites present on the adult bees and causing the mites to die. Alternatively, the hop acids are consumed by the bees and enter their hemolymph, where they are subsequently consumed by the mites, thereby causing the mites to die.

In another approach, the powdered mixture is delivered to the hive within a semi-permeable pouch that resembles a "teabag". To rid the hive of this foreign object, the bees rip up the pouch, thereby releasing the powder. The powdered hop acids get onto the body of the adult bees and are distributed throughout the hive, thereby killing (or otherwise interfering with mite proliferation or survival) mites present on the bees and inhibiting the mite infestation.

Encapsulated formulations

In one approach, a hop derivative is provided in an encapsulated formulation (liquid or powder). Preferably, a hop derivative in liquid or powder form is encapsulated in a coating that breaks down slowly inside the beehive. The coating provides for the long-term release of the hop derivative. Preferably, the composition is released over the course of two to six weeks (e.g., two, three, four, five, six weeks). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a hop derivative or other compound specified above through the walls, capillary tubing which releases the compound out of an opening in the tubing, polymeric blocks of different shapes, e.g., strips, corrugated strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries. Encapsulation methods suitable for use in apiculture are described, for example, by Rieth et al., Journal of Apiculture Research 25(2):78-84 (1986).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of miticides. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative is placed into the hive where it subsequently contacts and kills the mites. Oil release substrates include vegetable and/or mineral oils. In one embodiment, the substrate also contains a surface active agent that renders the composition readily dispersable in water; such agents include wetting agents, emulsifying agents, dispersing agents, and the like.

Alternatively, miticides of the invention may also be formulated in a solid tablet and comprise (and preferably consist essentially of) an oil, a protein/carbohydrate material (preferably vegetable based), a sweetener and an active ingredient useful in the prevention or treatment of a parasitic infection in a honey bee. Methods for making such compositions are known in the art and are described, for example, in U.S. Patent Publication No. 20060008492 . In one embodiment the invention provides a solid tablet and comprises (and preferably consist essentially of) an oil, a protein/ carbohydrate material (preferably vegetable based), a sweetener and an active ingredient (e.g., hops a and/or B acid, or combinations or derivatives thereof) useful in the prevention or treatment of a mite infestation. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., parafins and petroleum jelly), and other water immiscible hydrocarbons (e.g., parafins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion. While the relative fraction of each portion making up the material may vary, the material should include at least a portion of carbohydrate and protein.

The tablets also contain between about 10-75% (10, 15, 20, 25, 50, 75%) by weight of a sweetener. As used herein, the term "sweetener" generally refers to both natural and artificial sweeteners. Preferably, the sweetener is a sugar such as glucose, fructose, sucrose, galactose, lactose, and reversed sugar. The sugar is preferably selected from the group consisting of granulated sugar (white sugar), brown sugar, confectioner's sugar, impalpable sugar, icing sugar, and combinations thereof. Alcohols such as glycerin and complex carbohydrates, such as starches may also be used as the "sweetener" ingredient. The sweetener is used primarily as an attractant for the insects, however the sweetener also helps to impart a granular structure to the tablets, especially when the sweetener is a sugar. As previously discussed, this granular structure permits the tablet to crumble over time upon the exertion of sufficient forces.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

Tablets according to the present invention are manufactured by mixing all of the ingredients together and then compressing the mixture into a tablet of desired shape and size for a particular application. Preferably, the tablet is discoid in shape with a diameter of between about 2-5 inches and a thickness of from about 0.5-2 inches. The pressing may be accomplished by a manual or automatic pressing device. The pressure exerted on the mixture should be sufficient so as to form the tablet into a self-sustaining body.

Methods of delivering an active ingredient to an insect according to the present invention comprise the steps of providing a solid tablet containing the active ingredient as previously described and placing the tablet in a location where the insect may come into direct contact therewith. In treating honeybees that are generally colonized in a manufactured bee hive, the tablet is preferably placed inside the hive.

Over the next several weeks after the tablet is placed into the hive, the bees chew and crumble the tablet exposing the active ingredient to the other bees. The crumbs fall through the brood box away from the honey supers. Preferably, the entire tablet is disintegrated in about 30-45 days.

Miticides of the invention can also be delivered in the form of syrups that are attractive to bees and induce feeding behavior. The syrups for use in the invention preferably comprise sugar and water. Particularly preferred are 50% w/v sucrose solutions. A liquid composition is formed by dispersing hops acids in a sugar syrup comprising 50% sucrose in water. The composition is used as a feed supplement for the bees and can be placed at a suitable location in or near a hive.

Miticides of the invention can also be delivered in packets suitable for inducing hygienic behavior in bees. Such packets are prepared by enclosing a fine powder of hops acids and sugar in a porous material capable of being torn apart by bees. Preferably, the porous material is made of waxed paper or filter paper. Suitable filter papers include those comprising abaca fibers, wood pulp and cellulose rayon fibers. If desired, the paper is coated with polyethylene mixed with copolymers, polypropylene mixed with copolymers or 100% polypropylene.

In other embodiments, miticides are prepared in a dusting composition or as a powder. Dusting compositions are typically prepared by grinding sugar to a fine powder and mixing it into the powder hops acids. Alternatively, the dusting compositions are prepared as described in Example 3 for maltodextrin, where the powder is obtained by spray drying. The skilled artisan adjusts the conditions used in the spray drying process to achieve particles or granules of a size that facilitates delivery to the bees. Desirably, the powder comprises fine particles that coat the bee and all of its body parts (e.g., joints, groove, bristles). The dusting composition can be applied directly to the top of the bee frames, to the combs within the hive, or to the interior surfaces of the hive, or may be applied directly to a bee cluster.

Alternatively, the miticides are prepared in a liquid spray composition that is formed by dispersing hops acids in any suitable liquid. Preferably, the hops acids are dispersed in water. If desired, the spray composition also includes a surfactant that allows the spray to be dispersed efficiently without clogging the spraying apparatus. The composition can be used to spray the hive interior, or the comb, or can be used to spray bee clusters directly.

In another approach, miticides of the invention are delivered in the form of a vapor. Methods for delivering such vapors to a hive are described, for example, in U.S. Patent Publication No. 20020151249.

Miticide Delivery

Figure 5:
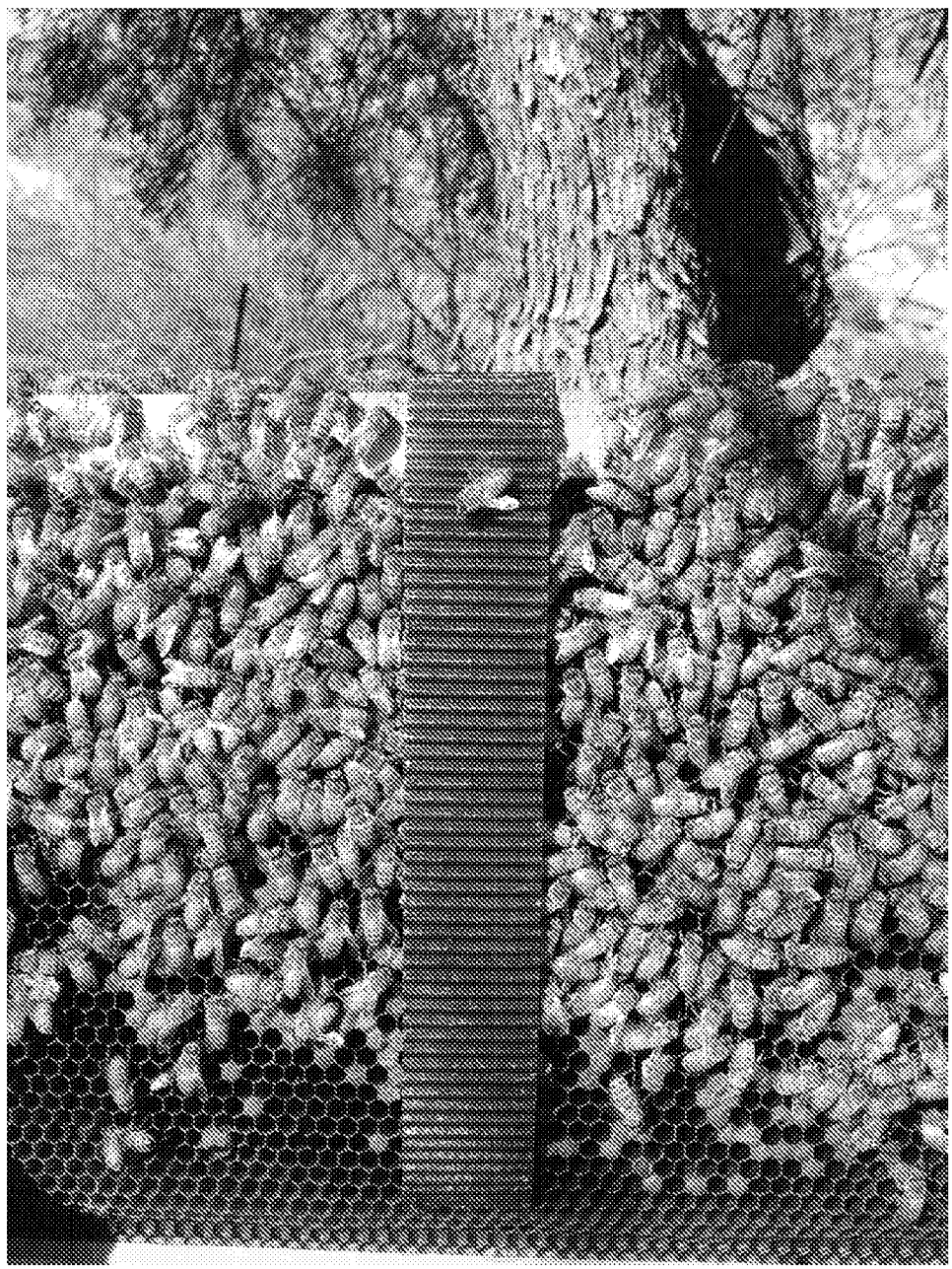
FIG. 5 provides a photograph of showing HopGuard II®® being used to treat hives.

Devices for delivering pest control agents to bees or to a bee hive are known in the art. In one embodiment, the invention provides corrugated strips that comprise beta acid resins, solvent (e.g. propylene glycol), and an emulsifier (e.g., polysorbate). The corrugated strips are typically soaked in a liquid composition comprising equal amounts of beta acid resins, solvent (e.g. propylene glycol), and an emulsifier (e.g., polysorbate). Such compositions are referred to as HopGuard II® (FIG. 5). HopGuard II® is distinguishable from standard HopGuard® (FIG. 1).

Figure 4:
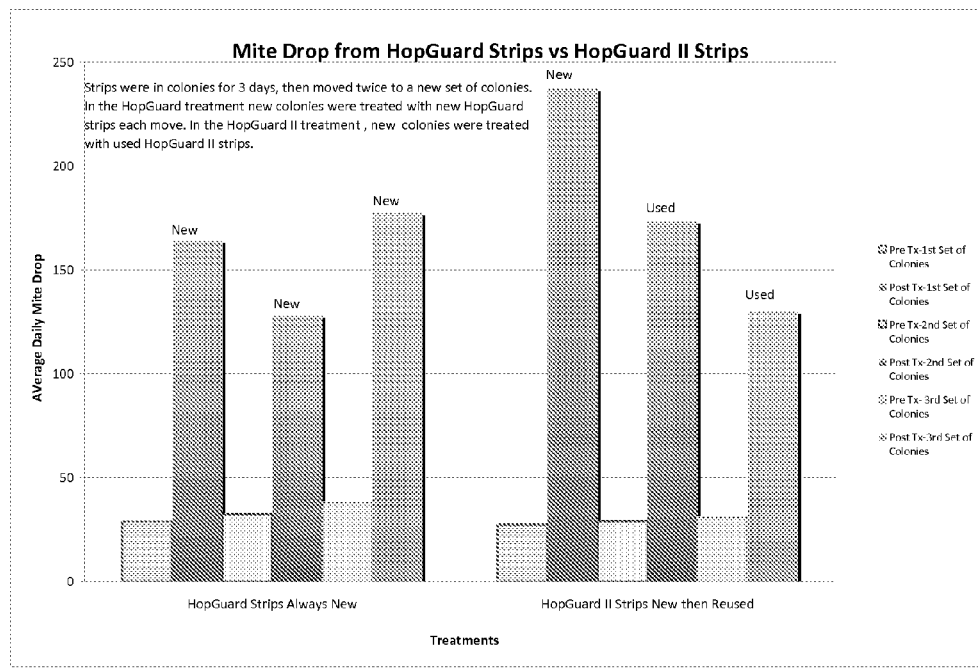
FIG. 4 is a graph showing mite drop in untreated hives (light blue, light red, light peach) or in hives treated with standard HopGuard® or HopGuard II®. For each condition, mites were collected on sticky boards for three days in each of five hives and the results were averaged.

Standard HopGuard® is produced by soaking card board strips in a liquid composition comprising beta acid resins, solvent (e.g. propylene glycol), and an emulsifier (e.g., polysorbate). As reported in more detail below, HopGuard II® shows superior delivery properties relative to standard Hop Guard. In particular, in HopGuard II® treated hives by day 3 90% of bees had detectable levels of hop beta acids, whereas less than 50% of bees in standard HopGuard® treated hives had detectable levels of hop beta acids at any time during the course of treatment. The amount of hop beta acids per bee was also significantly higher in HopGuard II® treated hives relative to hives treated with equivalent amounts of standard Hop Guard. HopGuard II® was effective longer than standard HopGuard® (FIG. 4).

Corrugated sheets useful in the methods of the invention are preferably single-faced sheets (i.e., cardboard having a plain sheet on one side to which a corrugated sheet is affixed). Preferably, corrugated cardboard useful in the methods of the invention are between about 1-2 mm in thickness and comprise preferably about 5, 6, 7, or 8 flutes per inch. In other embodiments, corrugated strips of the invention are about 1, 2, 3, 4, 5, 6, 7, 8, 9, 10 mm,15 mm,20 mm,30 mm,40 mm in thickness. Single wall and double wall honeycomb cardboard may be used.

In other embodiments, corrugated sheets have the following specifications are useful in the methods of the invention:

| Flute Designation | Flutes per linear foot | Flute thickness (in) | Flutes per linear meter | Flute thickness (mm) |
| --- | --- | --- | --- | --- |
| A flute | 33 +/− 3 | 3/16 | 108 +/− 10 | 4.8 |
| B flute | 47 +/− 3 | 1/8 | 154 +/− 10 | 3.2 |
| C flute | 39 +/− 3 | 5/32 | 128 +/− 10 | 4.0 |
| E flute | 90 +/− 4 | 1/16 | 295 +/− 13 | 1.6 |
| F flute | 128 +/− 4 | 1/32 | 420 +/− 13 | 0.8 |

Corrugated sheets useful in the methods of the invention may be single or double-faced and are made of paper-based material, engineered wood product comprising wood fibers, plastic, polymer, or any other material known in the art.

Other delivery devices include strips, corrugated strips, controlled release corrugated strips, tablets, reservoirs, polymer discs, trays, and evaporation devices. If desired, the delivery device is provided as biodegradable form. In one preferred embodiment, the invention provides biogradable corrugated strips comprising hop beta acids. Preferably, the strips are moistened with a liquid composition comprising about 16% potassium salts of hop beta acids. In one embodiment, the liquid composition is an emulsion comprising equal parts by weight (i.e., 33.3%) hop beta acid resins, propylene glycol, and polysorbate-60 . In other embodiments, the composition comprises equal amounts by volume. Moistened corrugated strips comprising hop beta acids are hung from the frame of a box hive. In one embodiment, treatment is carried out for 1, 2, 3, 5, 7, 10, 12, 14, 21, or 30 days. In another embodiment, treatment is carried out for 2, 3, 4, 5, 6, 8, 10, or 12 weeks. If desired, strips are replaced after they dry out. The treatment is repeated as necessary. Typically two strips/ten frames are used, although higher or lower numbers may be used. In one embodiment, the strips used were about 17" in length and 1¼" wide. In particular embodiments, the strips are biodegradable strips comprising fibers that readily absorb liquid. For example, the corrugated strips are made of paper, cardboard, chipboard, or other similar material. The strips are moistened with a liquid hop beta acid composition (e.g., 33.3% hop beta acid resins, 33.3% propylene glycol, 33.3% polysorbate-60 by weight) and are shipped or otherwise delivered to the end-use (e.g., hive keeper) in moisture-resistant foil packets. In one embodiment, the strips are about 1-2" (e.g., 1, 1.25, 1.5, 1.75, 2.0") in width by 1-2 feet (e.g., 12, 16, 18, 20, 24") in length.

For the treatment of packaged bees, corrugated strips comprising hop beta acids are hung in the bee packages during shipment. In particular, devices suitable for delivering a composition of the invention to a parasitic mite, to a honey bee, or to a honey bee hive are described, for example, in U.S. Patent Publication Nos. 20070059333; 20070026765; 20060141904; 20060009122; 20060008492; 20050095954; 20050090560; 20050048093; 20040229542; 20040077291; 20030190860; 20030044443; 20030027490; 20020182977; 20020151249; 20020094756; 20010014346 and 20020151249. Dispensing means and suitable compositions for controlled release are described in U.S. Pat. Nos. 6,843,985; 5,750,129; 4,775,534; 5,849,317; 5,348,511; 6,037,374; 7,137,864; 6,837,770; 6,820,773; 6,702,645; 6,646,014; 6,620,025; 6,595,828; 6,585,557; 6,475,061; 6,468,129; 6,277,371; 6,221,375; 6,204,283; 6,096,350; 6,037,374; 6,010,390; 5,312,622; 5,230,894; 5,227,162; 5,135,758; 5,070,091; 5,069,651; 5,023,359; 4,876,265; 4,867,731; 4,837,216; 4,682,380; and 4,299,816, which are incorporated herein by reference in their entirety.

Kits

The invention provides kits for the treatment or prevention of an acarid infestation. In one embodiment, the kit includes a composition (e.g., a corrugated strip) containing an effective amount of a hop derivative in a form suitable for delivery to a site of infestation (e.g., bee hive). In some embodiments, the kit comprises a container which contains a miticide; such containers can be boxes, ampoules, bottles, vials, tubes, bags, pouches, blister-packs, or other suitable container forms known in the art. Such containers can be made of plastic, glass, laminated paper, metal foil, or other materials suitable for holding miticides.

In one embodiment, the kit includes a composition containing an effective amount of a hop derivative in a form suitable for delivery to a site of infestation (e.g., bee hive). In some embodiments, the kit comprises a container which contains a miticide; such containers can be boxes, ampoules, bottles, vials, tubes, bags, pouches, blister-packs, or other suitable container forms known in the art. Such containers can be made of plastic, glass, laminated paper, metal foil, or other materials suitable for holding miticides.

In particular embodiments, the invention provides a kit that features corrugated strips (e.g., paper, cardboard, chipboard, or other similar material or any other absorbent material known in the art) that are moistened, soaked, or otherwise impregnated with hop beta acids. For example, the corrugated strips comprise about 15-20% (e.g., 15, 16, 17, 18, 19, 20%) hop beta acids (e.g., HopGuard®) alone or in combination with other hop derivatives. In one embodiment, the corrugated strips comprise a controlled release composition for treating or preventing a parasitic mite infestation, the composition comprising an effective amount of a hop derivative in a suitable form for delivery to a honey bee parasitic mite. Preferably, the corrugated strips are in a biodegradable form. In one embodiment, the corrugated strips are pre-soaked in a hop acid composition and than packaged in foil, plastic, or similar materials to maintain the strips in a moist condition. If desired the miticide of the invention is provided together with instructions for administering it to a site of infestation. The instructions will generally include information about the use of the composition for the treatment or prevention of an acarid infestation. In other embodiments, the instructions include at least one of the following: description of the miticide; dosage schedule and administration for treatment or prevention of a miticide infestation; precautions; warnings; description of research studies; and/or references. The instructions may be printed directly on the container (when present), or as a label applied to the container, or as a separate sheet, pamphlet, card, or folder supplied in or with the container.

EXAMPLES

Example 1

Preparation of Strips for HopGuard® Delivery

Standard HopGuard and HopGuard II® were prepared as follows.

A hop beta acid composition comprising 33.3% potassium salts of beta acid resins, 33.3% propylene glycol, and 33.3% polysorbate-60 by weight was prepared. The hop beta acid composition was absorbed onto 17.5 inch long flat cardboard strips ("standard Hop Guard") or onto strips of fluted single-faced corrugated cardboard (HopGuard II®). The corrugated strips had about 7 flutes/inch and were about 2 mm thick. Strips were applied at the rate of two strips per 10-frame box. The folded strips were hung over the frames near the middle of the frame with one half of the strip on each side of the frame (FIG. 1A: Standard Hop Guard, FIG. 11: HopGuard II®). The application was repeated with a second strip hung over the adjacent center frame leaving some distance of 3-4 inches between the strip locations (FIG. 1B).

For testing purposes, the formulas were delivered in ten-frame colonies using cardboard strips that had been soaked for 24 hours in the hop composition.

Pre-treatment mite counts were monitored in all colonies including untreated control using the sticky board method. The treatments were placed in the colonies along with sticky boards and left for 72 hours after which the sticky boards were removed and the mites that had dropped to the boards were counted and the data recorded.

The mite drop counts are expressed as an average daily mite drop.

Example 2

HopGuard II® Provides Superior Delivery of Hop Beta Acids

The invention provides a new device ("HopGuard II®") that is surprisingly effective in delivering hop acid derivatives to honey bees for the treatment or prevention of parasitic mites (e.g., *Varroa* mites, tracheal mites). Unexpectedly, corrugated paper (e.g., corrugated cardboard) impregnated with hop beta acids delivered more active ingredient (e.g., beta acids) per bee and remained effective against honey bee parasitic mites for a longer period than standard paper strips. FIG. 2 and Table 2 show the amount of active ingredient per bee after the bees were exposed to HopGuard II over a ten day period.

TABLE 2

| In vivo Cardboard and Paper Study. Average µg Beta Acids ("BA") per Bee | | | | | | |
|---|---|---|---|---|---|---|
| | Day 1 | Day 2 | Day 3 | Day 4 | Day 8 | Day 10 |
| Treatment | BA/bee | BA/bee | BA/bee | BA/bee | BA/bee | BA/bee |
| Corrugated | 18.5 | 12 | 14.3 | 9 | 13 | 5.4 |
| HopGuard | 6.34 | 4 | 10.14 | 4.6 | 1.8 | |

The first day that the corrugated strips were used, the amount of hop beta acids per bee was three times higher on bees present in hives treated with HopGuard II®. The amount of active agent per bee remained higher throughout the treatment period and was present at higher levels for a longer period of time. At day 8, less than 2 µg hop beta acids per bee was present in hives treated with standard Hop Guard. In contrast, at day 8, bees treated with HopGuard II® had greater than 12 µg hop beta acids per bee. At day 10, the amount of hop beta acids per bee was undetectable in hives treated with standard Hop Guard, while hives treated with HopGuard II® had greater than 5 µg hop beta acids per bee.

Figure 3:
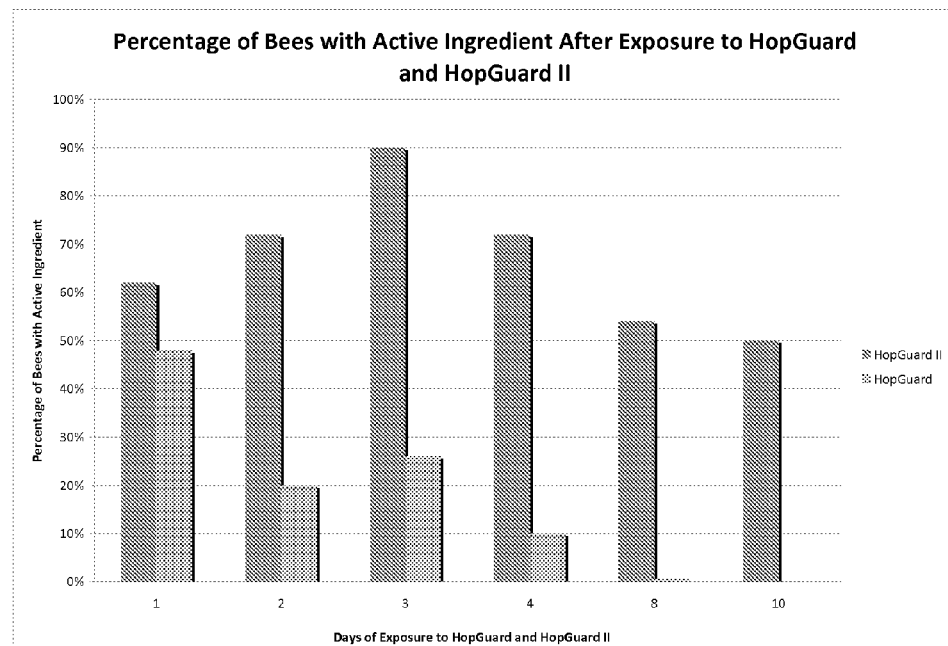
FIG. 3 is a graph showing the percentage of bees having detectable levels of hop beta acids. Bees were collected each day during a 10-day course of treatment with standard HopGuard® or HopGuard II®.

Not only were higher levels of hop beta acids present per bee in HopGuard II® treated hives, but as shown in Table 3 and FIG. 3 almost all bees present in hives treated with HopGuard II® showed detectable levels of beta acids.

TABLE 3

Average Percentage of bees with beta acids.

|  | Day 1 | Day 2 | Day 3 | Day 4 | Day 8 | Day 10 |
|---|---|---|---|---|---|---|
| Corrugated + | 62% | 72% | 90% | 72% | 54% | 50% |
| HopGuard + | 48% | 20% | 26% | 10% | 1% | |

More specifically, by day three, greater than 90% of bees present in hives treated with HopGuard II® showed detectable levels of hop beta acids (FIG. 3). In contrast, less than 30% of bees in hives treated with HopGuard II® showed detectable levels of hop beta acids at day 3 (FIG. 3). In fact, in hives treated with standard HopGuard® for ten days, less than 50% of bees showed detectable levels of hop beta acids at any point during the treatment (FIG. 3). Thus, HopGuard II® was more effective in distributing hop beta acids throughout the hive than standard Hop Guard.

The superior distribution of HopGuard II® resulted in good control of *Varroa* mites (FIG. 4). In this set of experiments, data was collected from each of 5 hives and averaged. Hives infested with *Varroa* mites were treated with standard HopGuard® or HopGuard II® for three days. While standard HopGuard® killed between 100-200 mites per day in each of five treated hives (FIG. 4). HopGuard II® killed close to 250 mites in the first hives treated for days 1-3. On day four, the "used" HopGuard II® strips were moved from the treated hives to a new set of five infested hives. The strips remained effective in controlling mites from days 4-6. The "used" HopGuard II® killed between 150-200 *Varroa* mites per day in the second set of five treated hives (FIG. 4). At day 7, the "used" Hop Guard II was moved into a third set of five infested hives. Between days 7-9, the "used" HopGuard II® killed between 100-150 mites per day (FIG. 4). Thus, even after 7-9 days of continuous use HopGuard II® remained as effective in killing mites as newly applied standard HopGuard® (FIG. 4).

FIG. 5 shows HopGuard II® in a hive.

Compounds of the invention are prepared in a manner essentially as described above and in the general schemes. The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. Another embodiment is a compound of any of the formulae herein made by a process delineated herein, including the processes exemplified in the schemes and examples herein. Another aspect of the invention is a compound of any of the formulae herein for use in as a miticide as delineated herein.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A corrugated strip for use in reducing a honey bee parasitic mite infestation in a hive, the strip comprising a liquid composition in an effective amount for distribution of potassium salts of hop beta acid resins to honey bees for at least ten days and comprising between about 30-35% by weight propylene glycol, about 30-35% by weight emulsifier, and about 30-35% by weight potassium salts of hop beta acid resins.

2. The corrugated strip of claim 1, wherein the liquid composition is a solution or an emulsion.

3. The corrugated strip of claim 1, wherein the liquid composition comprises equal parts potassium salts of hop beta acid resins, propylene glycol, and polysorbate 60.

4. The corrugated strip of claim 1, wherein the strip comprises paper, cardboard, or another paper pulp based material.

5. The corrugated strip of claim 1, wherein the strip is between about 1 and 3 mm thick and has between about 5 and 8 flutes per inch.

6. An absorbent corrugated strip comprising a liquid composition comprising between about 30-35% by weight propylene glycol, about 30-35% by weight emulsifier, and about 30-35% by weight potassium salts of hop beta acid resins.

7. A foil package comprising an absorbent corrugated strip in a liquid composition comprising between about 30-35% by weight propylene glycol, about 30-35% by weight emulsifier, and about 3035% by weight potassium salts of hop beta acid resins and wherein the foil package is a moisture resistant package.

8. A man-made hive comprising a corrugated strip for use in reducing a honey bee parasitic mite infestation, the strip comprising a liquid composition in an effective amount for distribution of hop beta acid resins to honey bees for at least ten days and comprising between about 30-35% by weight propylene glycol, about 30-35% by weight emulsifier, and about 30-35% by weight potassium salts of hop beta acid resins.

9. A method of reducing a honey bee parasitic mite infestation in a honey bee hive, the method comprising:
   contacting a hive with a corrugated strip for use in reducing a honey bee parasitic mite infestation, the strip comprising a liquid composition comprising between about 30-35% by weight propylene glycol, about 30-35% by weight emulsifier, and about 30-35% by weight potassium salts of hop beta acid resins;
   distributing hop beta acid resins to honey bees for at least ten days; and
   reducing a bee parasitic mite infestation in the hive.

10. The method of claim 9, wherein the method involves providing two corrugated strips per ten frames.

11. The method of claim 9, further comprising hanging the corrugated strips from a frame within the hive.

12. The absorbent corrugated strip of claim 6, wherein the strip is between about 1 and 3 mm thick and has between about 5 and 8 flutes per inch.

13. The foil package of claim 7, wherein the strip is between about 1 and 3 mm thick and has between about 5 and 8 flutes per inch.

14. The man-made hive of claim 8, wherein the strip is between about 1 and 3 mm thick and has between about 5 and 8 flutes per inch.

15. The method of claim 9, wherein the strip is between about 1 and 3 mm thick and has between about 5 and 8 flutes per inch.

16. The absorbent corrugated strip of claim 6, wherein the liquid composition is provided in an effective amount for distribution of potassium salts of hop beta acid resins to honey bees for at least seven days.

17. The corrugated strip of claim 5, wherein the strip is about 2 mm thick and has about 7 flutes per inch.

18. The absorbent corrugated strip of claim 12, wherein the strip is about 2 mm thick and has about 7 flutes per inch.

19. The foil package of claim 13, wherein the strip is about 2 mm thick and has about 7 flutes per inch.

20. The man-made hive of claim 14, wherein the strip is about 2 mm thick and has about 7 flutes per inch.

21. The method of claim 15, wherein the strip is about 2 mm thick and has about 7 flutes per inch.

22. The corrugated strip of claim 4, wherein the strip comprises cardboard and a corrugated sheet.

23. The absorbent corrugated strip of claim 6, wherein the strip comprises cardboard and a corrugated sheet.

24. The foil package of claim 7, wherein the strip comprises cardboard and a corrugated sheet.

25. The man-made hive of claim 8, wherein the strip comprises cardboard and a corrugated sheet.

26. The method of claim 9, wherein the strip comprises cardboard and a corrugated sheet.

* * * * *